United States Patent [19]

McKinney

[11] Patent Number: 4,485,256

[45] Date of Patent: Nov. 27, 1984

[54] DIMERIZING ACRYLATES TO HEXENEDIOATES USING RUTHENIUM COMPOUND CATALYSTS

[75] Inventor: Ronald J. McKinney, Wilmington, Del.

[73] Assignee: E. I. Du Pont de Nemours and Company, Wilmington, Del.

[21] Appl. No.: 470,537

[22] Filed: Feb. 28, 1983

[51] Int. Cl.$^3$ .......................................... C07C 67/343
[52] U.S. Cl. ..................... 560/202; 502/154; 502/169; 502/170; 502/230; 502/328; 502/330; 562/598
[58] Field of Search ................ 560/202; 502/154, 169, 502/170, 230, 328, 330

[56] References Cited

U.S. PATENT DOCUMENTS

| | | | |
|---|---|---|---|
| 2,244,645 | 6/1941 | Jacobson | 560/202 |
| 3,013,066 | 12/1961 | Alderson | 560/202 |
| 3,074,999 | 2/1963 | Rauhut | 560/202 |
| 3,227,745 | 1/1966 | McClure | 560/202 |
| 3,322,819 | 5/1967 | Schreyer | 560/202 |
| 3,548,021 | 12/1970 | Brattesani | 560/202 |
| 3,946,066 | 3/1976 | Todd | 260/465.8 D |
| 3,956,358 | 5/1976 | Onsager | 260/465.8 D |

FOREIGN PATENT DOCUMENTS

| | | |
|---|---|---|
| 796775 | 10/1968 | Canada. |
| 2211443 | 8/1974 | France. |
| 105115 | 9/1977 | Japan. |
| 1100350 | 1/1968 | United Kingdom. |
| 1355917 | 6/1974 | United Kingdom. |

OTHER PUBLICATIONS

Alderson, Jenner and Lindsey, *J. Am. Chem. Soc.*, 87, 5638, (1965).

*Primary Examiner*—Natalie Trousof
*Assistant Examiner*—Vera C. Clarke
*Attorney, Agent, or Firm*—James A. Costello

[57] ABSTRACT

Process for dimerizing alkyl acrylate esters to dialkyl hexenedioates in the presence of an alkali metal-treated or alkaline earth metal-treated ruthenium compound. The hexenedioate products are useful to prepare adipic acid.

27 Claims, No Drawings

DIMERIZING ACRYLATES TO HEXENEDIOATES USING RUTHENIUM COMPOUND CATALYSTS

BACKGROUND OF THE INVENTION

This invention concerns an improved ruthenium-catalyzed process for dimerizing alkyl acrylates to dialkyl hexenedioates. The latter compounds are readily convertible to adipic acid (hexanedioic acid) by hydrogenation and subsequent hydrolysis. Adipic acid is used to produce condensation polymers such as nylon 66.

U.S. application Ser. No. 485,943, a continuation-in-part of U.S. application Ser. No. 348,364, now abandoned, discloses a process for making dialkyl hexenedioates comprising dimerizing an alkyl acrylate of the formula $H_2C=CH-COOR$, wherein R is a straight chain alkyl group, in the presence of an alcohol and a ruthenium compound treated with one or more metals selected from the group consisting essentially of zinc, manganese, iron, cobalt, and copper, said ruthenium compound being in an oxidation state greater than zero, there being present optionally a phosphine and optionally a carboxamide.

Alderson, U.S. Pat. No. 3,013,066, and Alderson, Jenner, and Lindsey, *J. Am. Chem. Soc.*, 87, 5638 (1965), disclose the reaction of methyl acrylate in the presence of ruthenium chloride and methanol to give a mixture of products that includes dimethyl 2-hexenedioate.

Canadian Pat. No. 796,775 discloses the dimerization of alkyl acrylates in the presence of a mixed ruthenium compound-zinc catalyst, a hydrogen donor, and a phosphine.

U.S. Pat. No. 3,322,819 discloses dimerization of methyl methacrylate to a nonlinear product, dimethyl 2,2,4-trimethylglutarate, by heating with ruthenium carbonyl in the presence of water and carbon monoxide under pressure. In Example 2 the ruthenium compound that is charged is ruthenium trichloride, and the ruthenium carbonyl, $Ru(CO)_5$, is made in place. Ruthenium carbonyl is a compound of zerovalent ruthenium. This patent shows that a lower-valent ruthenium compound made by reducing $RuCl_3$ does not necessarily give linear products in the dimerization of an acrylic-type ester.

Japanese Patent Publication No. 52-105115 discloses nonlinear acrylic esters dimerized with a catalyst that is a mixture of a phosphorus compound (usually a phosphine); a compound of a metal of Group I, II, III, VI, VII, or VIII; and a divalent sulfur compound. In a list of 49 exemplary metal compounds, palladium chloride is the only compound of a Group VIII noble metal.

French Patent Publication No. 2,211,443 discloses linear derivatives of monounsaturated dicarboxylic acids of formula $ROC-CH_2-CH_2-CH=CH-COR$ (where R is lower alkoxy, aryloxy, acyloxy or aminated optionally substituted) and corresponding derivatives are prepared by dimerization of unsaturated carboxylic acid derivatives of formula $CH_2=CH-COR$ (where R is as above) using solution Pd(II) complex catalyst and a quinone co-catalyst, the reaction being effected at 0° to boiling point of the reaction medium and under normal pressure.

U.S. Pat. No. 3,548,021 discloses the oxidative dimerization of isobutylene to para-xylene using a Group VIII noble metal in an elevated oxidation state and a redox agent and oxygen to maintain the elevated oxidation state of the Group VIII metal.

U.S. Pat. No. 3,956,358 discloses the dimerization of acrylic esters to nonlinear esters of 2-methyleneglutaric acid in the presence of a catalyst comprising certain Group VIII metal halides, but not Ru halides.

U.S. Pat. No. 3,946,066 discloses a heterogeneous ruthenium catalyst for the dimerization and hydrodimerization of olefinically unsaturated compounds by co-precipitating a ruthenium compound with an aluminum oxide and/or hydroxide.

SUMMARY OF THE INVENTION

This invention concerns a process for making dialkyl hexenedioates without the presence of a hydrogen donor comprising dimerizing an alkyl acrylate of the formula $H_2C=CH-COOR$, where R is an alkyl group of up to about 18 carbon atoms, in the presence of a ruthenium catalyst whose formal oxidation state is lower than zero. The process of this invention can be run employing such a catalyst ab initio, or, such catalyst can be made in situ. Various methods can be employed to lower the oxidation state of the catalyst in situ. Such methods include treatment of a ruthenium compound with a composition containing one or more metals selected from the group consisting essentially of alkali and alkaline earth metals; electrochemical reduction of a ruthenium compound; and treatment of a ruthenium compound with strong alkali bases, e.g., NaOH (aq).

Although the identity of the alkyl group in the alkyl acrylate is not critical, lower alkyl acrylates are preferred because of their availability, and methyl acrylate and ethyl acrylate are especially preferred because of ease of isolation of the reaction products. Lower alkyl is defined as alkyl of up to and including eight carbons. For practical reasons, the alkyl group will seldom exceed about 2 or 3 carbons.

Contemplated ruthenium compounds of oxidation state less than zero can be generated in several ways. A preferred manner of treatment is to contact a ruthenium compound whose oxidation state is at least zero with an alkali and/or alkaline earth metal reducing agent. Typically, pretreatment oxidation states are from 0 to +4. Though not wishing to be bound hereby, it is believed that the post-treatment oxidation state is approximately −2. Ruthenium catalysts having oxidation states even lower than −2 may be operable in the process of this invention. Preferred ruthenium compounds have a pretreatment oxidation state of zero.

Reaction temperatures are usually between room temperature to about 200° C. However, slightly higher or lower temperatures may be employed. Typically, reactions are run at 50° C. to 200° C. with preferred temperatures being about 100° C. to 160° C.

The amount of ruthenium catalyst charged will depend largely on the amount of alkyl acrylate in the reaction mixture, and the ratio of moles of alkyl acrylate to gram atoms of ruthenium can vary widely. Usually, for efficient use of the ruthenium catalyst, the ratio will be above about 25/1 and up to 5000/1 or higher. Preferably, the ratio will be between 200/1 and 2500/1, and most preferably between 250/1 and 2000/1.

It is most preferred to incorporate one or more selected cyclic or acyclic polyether(s) in the reaction mixture. The most preferred embodiment of this invention comprises treating (benzene)bis(methyl acrylate)ruthenium in methyl acrylate with stoichiometric amounts of a solution of sodium naphthalide in tetrahydrofuran and then adding a stoichiometric amount of a polyether such as an acyclic polyethylene oxide, especially one having an average molecular weight of about 200, and heating in a closed system to about 140° C.

The process of this invention is characterized by high conversions (moles of alkyl acrylate consumed divided by moles of alkyl acrylate charged), by good selectivity (moles of alkyl acrylate converted to linear dimer divided by moles of alkyl acrylate consumed), relatively low incidence of by-product formation, and relatively simple separation and purification steps during product isolation.

DETAILS OF THE INVENTION

The Ruthenium Catalyst

The treating metals, if needed to lower the oxidation state, can be added along with the ruthenium compound to the reactant mixture. Then, the reaction can be run at reaction temperatures. Alternatively, the reactant mixture including ruthenium compound, can be pretreated with the metal which is removed before applying reaction temperatures.

The pretreatment ruthenium compound can be any such compound in which the ruthenium is in an oxidation state of zero or greater and is at least slightly soluble in the reaction mixture, i.e., at least about 0.01%. When the oxidation state of the ruthenium is greater than 0, the compound will usually contain at least one more-or-less common anion associated with the ruthenium, such as halide, nitrate, sulfate, or carboxylate. Preferably, such compounds will be free of chelating anions such as 1,3-diketonate. A zerovalent ruthenium compound will preferably be free of carbonyl (CO) and phosphine ligands and contain at least one carboalkoxy-substituted hydrocarbon ligand such as methyl acrylate or dimethyl muconate.

Examples of operable pretreatment ruthenium compounds are ruthenium dichloride, ruthenium trichloride, ruthenium tetrachloride, ruthenium tribromide, ruthenium triiodide, ruthenium nitrate, ruthenium acetate, ruthenium naphthenate, ruthenium stearate, benezeneruthenium dichloride, tetrakis(benzonitrile)ruthenium dichloride, bicycloheptadieneruthenium dibromide, diruthenium tetrabutyrate dichloride, benzenebis(methyl acrylate)ruthenium, benzenebis(ethyl acrylate)ruthenium, bis(dimethyl muconate) (trimethyl phosphite)ruthenium, bis(dimethyl muconate)carbonylruthenium.

Preferred pretreatment ruthenium compounds are those in an oxidation state of zero. Such compounds are characterized by good solubility in typical reaction mixtures, by being relatively noncorrosive to metal reaction vessels, and by requiring relatively small amounts of alkali and/or alkaline earth metals for conversion to active catalyst species. The most preferred of the zerovalent compounds are benzenebis(methyl acrylate)ruthenium and benzenebis(ethyl acrylate)ruthenium.

As noted heretofore, isolable ruthenium compounds having oxidation state(s) less than zero can be used in the process of this invention without further treatment to lower their oxidation state. For instance, Example 18 illustrates use of one such compound having an oxidation state of $-2$.

Treating Metals

One criterion for an operable alkali- and/or alkaline earth-metal composition is that it be capable of reducing the oxidation state of ruthenium from a starting value of 0 to $+4$ to a final value of less than zero and down to what is believed to be a final value of approximately $-2$. Whether a metal-containing composition has this power can be determined independently by measuring its electrochemical potential for this particular reaction. For this purpose, there can be used a small (25 to 40 cc) electrochemical H cell the two sides of which are separated by a glass frit and modified to allow the contents to be kept under inert atmosphere, with platinum electrodes. The solution medium is 0.4M naphthalene/tetrahydrofuran. The material whose potential is to be measured is dissolved in one side of the H cell and the potential between the two sides is measured with a very sensitive voltmeter. If the material to be measured is insoluble, e.g., an amalgam, one of the platinum electrodes is put directly in contact with the amalgam and the potential difference is measured. Metals electroplated onto a platinum electrode could also be measured this way.

In this way, the following Table of electrochemical potentials has been developed. The more positive the potential, the better the reducing agent. In the Table, the term "naphNa" refers to naphthalenesodium, $C_{10}H_8Na$. This known composition and the others like it, e.g., "naphK" and "naphLi" are made in place by adding the particular metal to the naphthalalene-THF solution. The term "Na/Hg" and those that correspond to it, e.g., K/Hg, Ba/Hg, and the like, designate several known amalgams. "Ru(O)" designates the compound benzenebis(methyl acrylate)ruthenium(O).

TABLE 1

| Metal Composition | Electrochemical Potential (Volts) |
| --- | --- |
| naphNa | 2.7 |
| naphK | 2.7 |
| naphLi | 2.5 |
| K/Hg | 2.1 |
| Na/Hg | 2.0 |
| Ba/Hg | 1.8 |
| Ca/Hg | 1.5 |
| Mg/Hg | 1.2 |
| Mn/Hg | 0.7 |
| Zn/Hg | 0.6 |
| Ru(O) | 0.1 |
| Cu | 0.1 |

A composition that exhibits a potential of at least about 1.2 volt and higher in this test will be an acceptable reducing agent. The preferred compositions are the naphthalene(alkali metals) and amalgams of alkali metals and alkaline earth metals. The preferred metals are lithium, sodium and calcium. These give better selectivities to dimers, as opposed to higher oligomers, than do other Group Ia and IIa metals of higher atomic weight (and correspondingly higher ionic radius).

As noted above in the "Background" section, certain prior art such as Canadian Pat. No. 796,775 discloses catalysts comprising zinc metal-treated ruthenium compounds. In connection with that disclosure and similar disclosures it is noted that zinc treatment of the ruthenium pretreatment catalysts employed in the process of this invention would not reduce their oxidation states to less than zero. Zinc has insufficient reducing power to effect the lower oxidation states that characterize the ruthenium catalysts employed in the process of this invention. Another distinction versus said Canadian patent is that phosphines are not desired components of the instant dimerization process.

The amount of metal composition used to treat the ruthenium catalyst will depend on the valence of the treating metal (1 for alkali metals and 2 for alkaline-earth metals) and the oxidation state of the ruthenium in the charged ruthenium compound. Usually, a stoichiometric amount or a slight excess (about 5%) of treating metal is used when the composition is soluble in the reaction mixture, as is, for example, naphthalenesodium. The stoichiometric amount is given by the equation: gram/atoms of treating metal=(oxidation state of Ru+2)/valence of treating metal. When the treating composition is insoluble, as is, for example, sodium amalgam, an excess can be used, to insure complete treatment, and the unused composition can be recovered by conventional means, but a stoichiometric amount is preferred.

If the ruthenium compound contains a carboalkoxy substituted hydrocarbon ligand such as methyl acrylate, the alkyl acrylate can be added to the reaction system before or after the treatment with added-metal compositions; in the absence of such a ligand, alkyl acrylate must be present at the time of added-metal treatment.

A solvent in addition to the alkyl acrylate is not necessary. If desired, however, an inert solvent can be employed. Operable solvents include cyclohexanone, tetrahydrofuran (THF), and selected carboxamides. Useful carboxamides are acyclic aliphatic carboxamides of up to about eight carbons and intracyclic aliphatic carboxamides of up to about 16 carbons. Examples are dimethylformamide, diethylformamide, dipropylformamide, dimethylacetamide, dipropylacetamide, N-methylpyrrolidone, N-butylpyrrolidone, N-(2-ethylhexyl)pyrrolidone, and N-dodecylpyrrolidone.

A further increase in selectivity can be realized by incorporating a cyclic or acyclic polyether containing a plurality of $[-(CRR')_n-O-]$ units in the reaction mixture (where $n>0$, and R and R' can be H, alkyl or aryl units); the carbon framework can also be comprised of aromatic units such as ortho-phenylene units $[-ortho-C_6H-O-])$. Polyethers containing ethyleneoxy ($-CH_2-CH_2-O$) units are preferred. Examples are acyclic polyethylene oxides, e.g., Carbowax®, and cyclic "crown" ethers such as 1,4,7,10,13,16-hexaoxycyclooctadecane (more commonly known as "18-crown-6").

The following Examples illustrate the invention. All preparative manipulations were carried out under an atmosphere of nitrogen in a Vacuum/Atmosphere Corp. dry box. Tetrahydrofuran was distilled from benzophenone/sodium under nitrogen. N-methylpyrrolidone was treated first with potassium hydroxide and then distilled under vacuum from barium oxide. Methyl acrylate and other solvents were stored over activated 4 Å sieves. All solvents were sparged with nitrogen prior to use. The reaction mixtures described below were sealed by torch in heavy-walled glass ampoules under vacuum at liquid nitrogen temperature, and then submerged in an oil bath. Each ampoule was cooled in a water bath and opened to the air; completely quenching the reaction.

Reaction mixtures were analyzed by gas chromatography (GC) [HP5710A, FID; column 10% SE30 on kieselguhr silica ("Anakrom" ABS, 80/90 mesh) 12'×⅛" or 10% SE30 on kieselguhr silica ("Supelcoport", 80/90 mesh) 10'×⅛"] and product concentrations calculated by computer measurement of integrated peak areas and applying appropriate response factors and comparing against the internal standard decane or nonane. Molar response factors were found to be linear upon comparison between acrylate and dimer or adipate (1:0.5) and were therefore assumed to be linear for trimer, tetramer, etc. Percent area of a specific gas chromatograph peak was multiplied by the following relative molar response factors to obtain actual concentrations: dimer, 1.00; trimer, 0.66; tetramer, 0.50; pentamer, 0.40; hexamer, 0.33

Identities of the products were determined by mass spectral analyses of gas chromatographic effluents (GC-MS), and identities of isomers by comparing GC retention times against those of authentic samples.

EXAMPLE 1

Benzenebis(methyl acrylate)ruthenium was prepared by treating $[(C_6H_6)RuCl_2]_2$ with $AgBF_4$ in $CH_3CN$, filtering, and isolating the intermediate by precipitating with ether. The intermediate was treated with zinc powder in methyl acrylate and methanol and worked up by filtration, stripping under vacuum, extracting with ether/hexane, and crystallizing from the extract.

An unweighed amount of benzenebis(methyl acrylate)ruthenium(O) dissolved in N-methylpyrrolidone was treated with excess 1% Na/Hg. The yellow solution turn red. The red solution was decanted from the Na/Hg into methyl acrylate. The mixture was heated at 140° C. for 3 h. GC analysis revealed moderate conversion with a high dimer-to-trimer ratio. Hydrogenation of the mixture over Pd/C revealed a linear-to-branched ratio of 99:1 for the dimers.

EXAMPLE 2

A mixture of benzenebis(methyl acrylate)ruthenium(O) (0.050 g, 0.14 mmol), N-methylpyrrolidone (5 cc) and decane (0.20 cc) was treated with 1% Na/Hg. The red supernatant liquid was decanted and treated with methyl acrylate (10 cc). Aliquots were sealed under vacuum and heated at 140° C. Results are given in Table 2. Products were confirmed by GC-MS on the 180-min sample.

The trimer that was formed contained substantially no dehydrotrimer, and substantially no methyl propionate was formed. If dehydrotrimer were formed, the hydrogen lost would be expected to react with methyl acrylate to give methyl propionate. GC-MS also showed the presence of small amounts of pentamer and of methyl β-methoxypropionate. The column heading, "mol/Ru" means the number of moles of that particular product per gram atom of ruthenium.

TABLE 2

| Time min | Dimer mol/Ru | Trimer mol/Ru | Tetramer mol/Ru |
|---|---|---|---|
| 30 | 41 | <1 | <1 |
| 60 | 79 | 2 | 2 |
| 90 | 112 | 4 | 4 |
| 120 | 137 | 8 | 8 |
| 180 | 166 | 12 | 12 |

EXAMPLE 3

A mixture of $RuCl_3 \cdot 3H_2O$ (0.05 g) in 10 cc of a solution comprised of N-methylpyrrolidone (95% v/v), decane (4% v/v) and methyl acrylate (1% v/v) was treated with 1 cc of 1% sodium amalgam for 0.5 h with stirring. After decanting and filtering, the solution was treated with an equal volume of methyl acrylate. A sample was heated at 140° C. for 2 h, resulting in dimers (105 mol/Ru) and trimers (12 mol/Ru).

EXAMPLE 4

In a manner similar to that described in Example 3, RuBr$_3$ (0.07 g) was treated with Na/Hg. After heating for 2 h, the reaction mixture contained dimers (42 mol/Ru) and trimers (5 mol/Ru).

EXAMPLE 5

A mixture of benzenebis(methyl acrylate)ruthenium(O) (0.035 g, 0.10 mmol) and tetrahydrofuran (4.0 cc) was treated dropwise during stirring with 0.2M naphthalenesodium/tetrahydrofuran (1.0 cc) solution; then methyl acrylate (5.0 cc) and decane (0.20 cc) were added. Aliquots were sealed in glass and heated at 140° C. GC analysis gave the results reported in Table 3.

TABLE 3

| Time min | Dimer mol/Ru | Trimer mol/Ru | Tetramer mol/Ru |
|---|---|---|---|
| 60 | 41 | 2 | 0 |
| 120 | 72 | 3 | 1 |
| 180 | 104 | 5 | 2 |

A small amount of methyl β-methoxypropionate was also detected in all samples. Hydrogenation of the 180-min sample revealed that the dimer linear-to-branched ratio was 19:1.

EXAMPLE 6

In a manner similar to that described in Example 5, a mixture was prepared except that the tetrahydrofuran was replaced by N-methylpyrrolidone. Heating at 140° C. yielded the results reported in Table 4.

TABLE 4

| Time min | Dimer mol/Ru | Trimer mol/Ru | Tetramer mol/Ru |
|---|---|---|---|
| 60 | 102 | 8 | 8 |
| 120 | 125 | 28 | 19 |
| 180 | 125 | 30 | 20 |

Hydrogenation of the 120-min sample revealed a dimer linear-to-branched ratio of 49:1.

EXAMPLE 7

A mixture of RuCl$_3$.3H$_2$O (0.026 g, 0.10 mmol), methyl acrylate (5.0 cc), N-methylpyrrolidone (3.0 cc) and decane (0.20 cc) was treated dropwise very slowly during stirring with 0.4M naphthalenesodium/tetrahydrofuran (2.0 cc). Not all of the ruthenium compound dissolved and therefore some remained unreacted. The solution was decanted and aliquots were heated at 140° C. Results are reported in Table 5.

TABLE 5

| Time min | Dimer mol/Ru | Trimer mol/Ru | Tetramer mol/Ru |
|---|---|---|---|
| 60 | 40 | 1 | 1 |
| 120 | 89 | 6 | 6 |
| 180 | 117 | 12 | 12 |

Small amounts of methyl β-methoxypropionate and higher oligomers were also detected.

EXAMPLE 8

A mixture of benzenebis(methyl acrylate)ruthenium(O) (0.035 g, 0.10 mmol) methyl acrylate (10 cc), N-methylpyrrolidone (10 cc) and nonane (0.40 cc) was treated dropwise with 0.4M naphthalenelithium/tetrahydrofuran (0.50 cc) and aliquots were heated at 140° C. Results are reported in Table 6.

EXAMPLE 9

In a manner similar to that described in Example 8, a mixture was prepared and reacted using 0.4M sodium naphthalenesodium/tetrahydrofuran instead of naphthalenelithium. Results are reported in Table 6.

EXAMPLE 10

In a manner similar to that described in Example 8, a mixture was prepared and reacted using 0.45M naphthalenepotassium/tetrahydrofuran (0.40 cc) instead of naphthalenelithium. Results are reported in Table 6.

TABLE 6

| Time min | Dimer mol/Ru | Trimer mol/Ru | Tetramer mol/Ru | Pentamer mol/Ru | Hexamer mol/Ru |
|---|---|---|---|---|---|
| Example 8 | | | | | |
| 60 | 44 | 2 | 2 | <1 | <1 |
| 120 | 98 | 6 | 4 | 1 | 1 |
| 180 | 176 | 20 | 8 | 2 | <1 |
| Example 9 | | | | | |
| 60 | 66 | 4 | 4 | 3 | 1 |
| 180 | 210 | 48 | 33 | 10 | 4 |
| Example 10 | | | | | |
| 60 | 37 | 7 | 7 | 3 | 3 |
| 120 | 56 | 12 | 16 | 8 | 5 |
| 180 | 56 | 16 | 21 | 13 | 9 |

EXAMPLE 11

A mixture of benzenebis(methyl acrylate)ruthenium(O) (0.035 g, 0.10 mmol), methyl acrylate (16.0 cc), N-methylpyrrolidone (4.0 cc) and nonane (0.40 cc) was treated with 1/2% Ca/Hg (1 cc) for 0.5 h with stirring and then decanted, and aliquots were heated at 140° C. Results are reported in Table 7.

EXAMPLE 12

A mixture similar to that described in Example 11 was treated with 1/2% Ba/Hg instead of Ca/Hg. Results are reported in Table 7.

TABLE 7

| Time min | Dimer mol/Ru | Trimer mol/Ru | Tetramer mol/Ru | Pentamer mol/Ru | Hexamer mol/Ru |
|---|---|---|---|---|---|
| Example 11 | | | | | |
| 60 | 54 | 3 | 3 | 2 | <1 |
| 120 | 79 | 6 | 6 | 3 | 1 |
| Example 12 | | | | | |
| 60 | 22 | 9 | 6 | <1 | <1 |
| 120 | 38 | 12 | 9 | 2 | <1 |

EXAMPLES 13 TO 17

Examples 13 to 17 illustrate the use of a polyether in the reaction mixture, both in the presence of solvent (N-methylpyrrolidone) and the absence of any other solvent.

EXAMPLE 13

A mixture of benzenebis(methyl acrylate)ruthenium(O) (0.018 g, 0.05 mmol), methyl acrylate (5.0 cc), N-methylpyrrolidone (5.0 cc) and nonane (0.20 cc) was treated dropwise with 0.4M naphthalenesodium/tetrahydrofuran (0.25 cc) and then 18-crown-6 polyether (cyclic(—CH$_2$CH$_2$O—)$_6$, 0.026 g, 0.10 mmol) was added. Aliquots were heated at 140° C. Results are reported in Table 8.

TABLE 8

| Time min | Dimer mol/Ru | Trimer mol/Ru | Tetramer mol/Ru | Pentamer mol/Ru | Hexamer mol/Ru |
|---|---|---|---|---|---|
| 60 | 64 | 3 | 0 | 0 | 0 |
| 120 | 115 | 10 | 8 | 3 | 0 |
| 180 | 205 | 37 | 22 | 6 | 2 |

EXAMPLES 14 AND 15

A mixture of benzenebis(methyl acrylate)ruthenium(O) (0.035 g, 0.1 mmol) and methyl acrylate (5.0 cc) was treated dropwise with naphthalenesodium/tetrahydrofuran (0.4M, 0.55 cc). More methyl acrylate (14.0 cc) and nonane (0.40 cc) were added. The mixture was divided into two equal portions, and one portion treated with 18-crown-6 polyether (0.05 g) (about 4 equivalents/Ru). Aliquots were sealed under vacuum and heated at 140° C. Results are shown in Table 9.

TABLE 9

| Time min | Dimer mol/Ru | Trimer mol/Ru | Tetramer mol/Ru | Pentamer mol/Ru | Hexamer mol/Ru |
|---|---|---|---|---|---|
| Example 14 Without Crown Ether | | | | | |
| 30 | 17 | 1 | 0 | 0 | 0 |
| 60 | 37 | 2 | 2 | 0 | 0 |
| 180 | 158 | 6 | 5 | 2 | 1 |
| Example 15 With Crown Ether | | | | | |
| 30 | 31 | 1 | 3 | 0 | 0 |
| 60 | 74 | 3 | 5 | 0 | 0 |
| 180 | 200 | 9 | 11 | 4 | 1 |

EXAMPLES 16 AND 17

In a manner similar to that described in Example 15, a mixture was prepared and divided into two equal portions, except the second portion was treated with an acyclic polyethylene oxide, Carbowax ® 200 (0.10 g), instead of the crown ether. Aliquots were sealed under vacuum and heated at 140° C. Results are shown in Table 10.

TABLE 10

| Time min | Dimer mol/Ru | Trimer mol/Ru | Tetramer mol/Ru | Pentamer mol/Ru | Hexamer mol/Ru |
|---|---|---|---|---|---|
| Example 16 Without Acyclic Ether | | | | | |
| 30 | 19 | 1 | 1 | 0 | 0 |
| 60 | 38 | 2 | 1 | 0 | 0 |
| 180 | 126 | 6 | 5 | 2 | 1 |
| Example 17 With Acyclic Ether | | | | | |
| 30 | 31 | 2 | 1 | 0 | 0 |
| 60 | 88 | 4 | 3 | 1 | 0 |
| 180 | 194 | 10 | 7 | 3 | 0 |

EXAMPLE 18

A mixture of disodiumtetracarbonylruthenium (−II) (0.026 g, 0.10 mmol) prepared according to the literature, methyl acrylate (10 cc), N-methylpyrrolidone (10 cc), and nonane (0.40 cc) was prepared. Aliquots of the solution were heated at 149° C. Results are summarized in Table 11.

TABLE 11

| Time min | Dimer mol/Ru | Trimer mol/Ru | Tetramer mol/Ru | Pentamer mol/Ru | Hexamer mol/Ru |
|---|---|---|---|---|---|
| 60 | 11 | <1 | 0 | 0 | 0 |
| 160 | 90 | 18 | 30 | 12 | 3 |
| 230 | 106 | 29 | 54 | 18 | 6 |

Comparative Examples A to C demonstrate relatively poor dimerization employing ruthenium compounds in an oxidation state of zero compared to that achieved in the dimerization process of Example 6.

COMPARATIVE EXAMPLE A

A mixture of $RuCl_3 \cdot 3H_2O$ (0.026 g, 0.10 mmol), N-methylpyrrolidone (5.0 cc), methyl acrylate (5.0 cc) and decane (0.20 cc) was heated at 140° C. for 1 h. Product analysis is reported in Table 12.

COMPARATIVE EXAMPLE B

A mixture of $RuCl_3 \cdot 3H_2O$ (0.052 g, 0.20 mmol), N-methylpyrrolidone (9.0 cc), methyl acrylate (10.0 cc), nonane (0.40 cc), methanol (1.0 cc) and hydroquinone (0.01 g) was divided in half and heated at 140° C. for 1 h. See Table 12.

COMPARATIVE EXAMPLE C

In a manner similar to that employed in Comparative Example A, benzenebis(methyl acrylate)ruthenium(O) (0.035 g, 0.10 mmol) was reacted with methyl acrylate in N-methylpyrrolidone and decane at 140° C. for 1 h. See Table 12.

TABLE 12

| Example | Catalyst | Dimer Moles/Ru (Linear:Branched) | Trimer mol/Ru | Tetramer mol/Ru |
|---|---|---|---|---|
| A | $RuCl_3$ | 0 | 0 | 0 |
| B | $RuCl_3$ + MeOH | 0 | 0 | 0 |
| C | $(C_6H_6)(MA)_2Ru(O)$ | 20(9:1) | 8 | 0 |
| 6 | $(C_6H_6)(MA)_2Ru(O)$ + $C_{10}H_8Na$ | 102(49:1) | 8 | 8 |

The embodiments of the invention in which an exclusive property or privilege is claimed are defined as follows:

1. A process for making dialkyl hexenedioates in the absence of a hydrogen donor comprising dimerizing an alkyl acrylate of the formula, $H_2C=CH-COOR$, wherein R is an alkyl group of up to about 18 carbons, in the presence of a ruthenium catalyst whose formal oxidation state is lower than zero.

2. A process according to claim 1 wherein the ruthenium catalyst is made in situ by treating a ruthenium compound with a starting oxidation value of 0 to +4 with a composition containing at least one metal selected from the group consisting essentially of alkali metals and alkaline earth metals, said composition having an electrochemical potential of at least about 1.2 volts.

3. A process according to claim 1 wherein R is alkyl of up to eight carbons.

4. A process according to claim 3 wherein R is alkyl of up to three carbons.

5. A process according to claim 2 wherein the metal is selected from the group consisting essentially of sodium, lithium and calcium.

6. A process according to claim 2 wherein the metal-containing composition is selected from at least one member of the group consisting of naphthalene (alkali metal) compositions, metal amalgams of at least one alkali metal, and metal amalgams of at least one alkaline earth metal.

7. A process according to claim 6 wherein the metal-containing composition is naphthalene sodium, naphthalene potassium or naphthalene lithium.

8. A process according to claim 7 wherein the metal-containing composition is naphthalene sodium.

9. A process according to claim 7 wherein the metal-containing composition is naphthalene lithium.

10. A process according to claim 6 wherein the metal-containing composition is a metal amalgam of an alkali metal.

11. A process according to claim 10 wherein the alkali metal is sodium.

12. A process according to claim 10 wherein the alkali metal is potassium.

13. A process according to claim 10 wherein the alkali metal is lithium.

14. A process according to claim 6 wherein the metal-containing composition is a metal amalgam of an alkaline earth metal.

15. A process according to claim 14 wherein the alkaline earth metal is calcium.

16. A process according to claim 1 comprising dimerizing the alkyl acrylate in the presence of a polyether.

17. A process according to claim 16 wherein the polyether comprises ethyleneoxy units.

18. A process according to claim 2 comprising dimerizing the alkyl acrylate in the presence of a polyether.

19. A process according to claim 18 wherein the polyether comprises ethyleneoxy units.

20. A process according to claim 6 comprising dimerizing the alkyl acrylate in the presence of a polyether.

21. A process according to claim 20 wherein the polyether comprises ethyleneoxy units.

22. A process according to claim 6 wherein the ruthenium has a starting oxidation value of zero.

23. A process according to claim 22 comprising dimerizing the alkyl acrylate in the presence of a polyether.

24. A process according to claim 23 wherein the polyether comprises ethyleneoxy units.

25. A process according to claim 24 comprising dimerizing methyl acrylate in the presence of benzenebis(methyl acrylate)ruthenium treated with naphthalenesodium.

26. A process according to claim 24 comprising dimerizing methyl acrylate in the presence of ruthenium trichloride treated with naphthalenesodium.

27. A process according to claim 24 comprising dimerizing ethyl acrylate in the presence of benzenebis(ethyl acrylate)ruthenium treated with naphthalenesodium.

* * * * *